United States Patent [19]

Haag et al.

[11] 3,954,883

[45] May 4, 1976

[54] CATALYTIC POLYSTEP REACTIONS

[75] Inventors: Werner O. Haag, Trenton; Darrell Duayne Whitehurst, Titusville, both of N.J.

[73] Assignee: Mobil Oil Corporation, New York, N.Y.

[22] Filed: May 10, 1974

[21] Appl. No.: 468,850

Related U.S. Application Data

[63] Continuation of Ser. No. 57,796, July 23, 1970, abandoned, which is a continuation-in-part of Ser. No. 672,008, Oct. 2, 1967, abandoned.

[52] U.S. Cl............ 260/614 AA; 260/418 R; 260/491; 260/615 AA; 260/617 R; 260/617 HF; 260/604 HF; 260/631 H; 260/631 R; 260/638 HF; 252/430
[51] Int. Cl.$^2$........................... C07C 41/10
[58] Field of Search....... 260/614, 614 AA, 615 AA, 260/615 A; 252/430

[56] References Cited
UNITED STATES PATENTS

| | | | |
|---|---|---|---|
| 2,827,494 | 3/1958 | Brown et al. | 260/615 |
| 2,861,045 | 10/1952 | Langer | 260/614 X |
| 3,170,958 | 2/1965 | Howard | 260/614 X |
| 3,855,307 | 12/1974 | Rony et al. | 260/614 R |

OTHER PUBLICATIONS

Howard et al., J. Org. Chem., 26 (1961) pp. 1026–1028.

Lorette et al., J. Org. Chem., 24 (1959) pp. 1731–1733.

Sussman, Ind. Eng. Chem., 38 (1949) pp. 1228–1230.

*Primary Examiner*—Howard T. Mars
*Attorney, Agent, or Firm*—Charles A. Huggett; Michael G. Gilman

[57] ABSTRACT

This specification discloses a method for carrying out catalytic polystep organic reactions at low temperature. The method is applicable to reactions wherein an initial reactant forms at least one intermediate product in one step of the reaction and an intermediate product forms a desired product in another step of the reaction. One of these steps is catalyzed by an acid group or a basic group and another step is catalyzed by a metal group or a metal compound group. The reaction is carried out by contacting the initial reactant with an ion exchange resin containing chemically bonded thereto as catalytic sites an acid group or a basic group and containing finely dispersed therein as catalytic sites at a distance from the other catalytic sites of the order of molecular dimensions a metal group or a metal compound group.

5 Claims, No Drawings

CATALYTIC POLYSTEP REACTIONS

CROSS REFERENCE TO RELATED APPLICATIONS

This application is a continuation-in-part of copending application Ser. No. 57,796 filed July 23, 1970, and now abandoned, which in turn is a continuation-in-part of application Ser. No. 672,008, filed Oct. 2, 1967, now abandoned.

Catalysts useful in the invention are disclosed, together with their preparation, in copending application Ser. No. 22,362, filed Mar. 24, 1970, a continuation-in-part of application Ser. No. 647,221, filed June 19, 1967 and now abandoned, and copending application Ser. No. 34,863, filed May 5, 1970, a continuation-in-part of application Ser. No. 647,222, filed June 19, 1967 and now abandoned.

BACKGROUND OF THE INVENTION

1. The field of the invention comprises catalytic polystep organic reactions.
2. Reactions of this kind are known, comprising hydrocarbon transformations in the presence of catalysts such as intimate mixtures of a porous solid oxide like alumina and a metal like platinum, but they are carried out at elevated temperatures, at least above 200° or 300° C., and in the vapor phase. The catalytic reforming of petroleum naphtha to produce high octane gasoline is a typical example. So far as is known, the conduct of catalytic polystep organic reactions at low temperatures, in the liquid phase, and in the presence of catalysts as disclosed herein, is new.

SUMMARY OF THE INVENTION

Catalytic polystep organic reactions are carried out at low temperatures in the liquid phase by employing a polyfunctional catalyst made from an organic polymer and having two or more different types of sites, each type being capable of catalyzing a reaction step different from that catalyzed by another type of site. The different types of sites are separated by distances of the order of molecular dimensions.

DESCRIPTION OF THE SPECIFIC EMBODIMENTS

The reactions contemplated by the invention may be set forth in more or less general terms, and in this respect it is to be understood that the invention is not to be limited by theories. The kind of reaction, or reaction mechanism, to which the invention applies is one comprising successive steps, each step being a reaction carried out over a single type of catalyst site. Thus, a sequence of steps, and therefore at least one chemical intermediate product, are involved. The occurrence of successive reaction steps may be seen to involve the mediation of at least one intermediate product, and these intermediate products are believed to exist as true compounds, although some times at undetected concentrations. By a true compound is meant a normal chemical species that exists independently of, and is desorbed from, the catalyst and that is subject to ordinary physical laws of diffusion. The applicable reactions are herein designated catalytic polystep reactions and may include acid-catalyzed reactions, base-catalyzed reactions, metal-catalyzed reactions, and metal compound-catalyzed reactions, examples of which are noted hereinafter.

The catalysts intended for use in the reactions are characterized by having two or more types of sites that are separated by the small distances described, each type catalyzing a single separate reaction step. The catalysts contain the sites in the form of an intraparticle dispersion. In the form of an intraparticle dispersion, these sites cannot be separated from each other by physical means, such as flotation, which would serve to separate a physical mixture of such sites.

The catalysts may be designated polyfunctional catalysts, where the term "function" refers to a type of site. Types of sites of particular interest are acid sites, basic sites, metal sites, and metal compound sites. Acid sites may catalyze such specific reactions as condensations, dehydrations, enolizations, polymerizations, isomerizations, alkylations, hydrations, etc.; basic sites may catalyze reactions like enolizations, isomerizations, additions to carbonyl-group containing compounds, condensations, etc.; metal sites may catalyze reactions such as dehydrogenation double bond isomerization, oxidations, hydrogenation, etc.; and metal compound sites may catalyze such reactions as cracking, vinyl group interchange between vinyl esters, conversion of olefins to vinyl esters, vinyl ethers, and vinyl halides, carbonylations, hydroformylations, olefin dimerizations, polymerization of dienes, hydration of acetylenes, decarboxylations, etc. Preferred catalysts contemplated herein are dual functional catalysts having acid and metal sites, or acid and metal compound sites.

Considering the catalysts in more detail, they comprise organic polymers preferably in the form of ion exchange resins having finely dispersed therein a metal of Groups IB and VIII of the periodic table and/or a metal compound of the type described below. Metal-containing resins may be prepared in several ways, as described in the said copending applications, usually by introducing a metal directly in and/or on the resin; for example, particles of the resin are brought in contact with a solution containing a metal pi-complex, the latter is decomposed to form elemental metal which then deposits in and on the resin particles, forming intraparticle dispersions of metal in the resin particle. Metal compounds may be introduced into the resin by various methods, including impregnation, ion exchange, and ligand exchange. When introduced by ion exchange or ligand exchange, the metal compounds are thought to be chemically bonded to the resin.

The ion exchange resin which is used to prepare the catalyst contains functional groups, i.e., acid groups in the case of a cation exchange resin and basic groups in the case of an anion exchange resin, and these groups of course are chemically bonded to the resin; they are present in the final catalyst, constituting acid or basic sites. The metal or metal compound moieties of the catalyst provide metal or metal compound sites which are separate from the acid or basic sites and are disposed at a distance from the latter which is of the order of molecular dimensions, i.e. up to several hundred Angstrom units. The initial ion exchange resin, which is preferably porous, may be a cation exchange resin containing such acidic functional groups as sulfonic acid, phenolsulfonic acid, phenol, phosphonic acid, carboxylic acid, etc., or it may be an anion exchange resin containing primary, secondary, tertiary, or quaternary amine groups, quaternary ammonium hydroxides, quaternary phosphonium hydroxides, tertiary sulfonium hydroxides, guanidine groups, dicyandiamidine groups, polyamine groups, pyridine groups, and other organic nitrogen-containing basic groups. These ion exchange resins are generally made by subjecting to appropriate chemical treatment a desired copolymer base material or matrix; for example, a styrene-divinylbenzene copolymer may be converted to a sulfonic acid cation exchange resin by sulfonation; or the resins may be made by reacting all ingredients together, thus a cation exchange resin of phenolic type can be prepared by reacting a phenol, an aldehyde, and a sulfonic acid. Illustrative ion exchange resins for making the catalysts include sulfonated copolymers of styrene and a divinylaromatic, phenolic methylene sulfonic acid resins, sulfonated coal, styrene-divinylbenzene copolymer containing dimethylaminomethyl groups, polystyrene sulfonic acid resins, cross-linked polyvinyl pyridine, a copolymerized mixture of phenol, formaldehyde, and triethylenetetramine, hydrolyzed styrene-divinylbenzene copolymers incorporating maleic anhydride, polyacrylic acid resin, chloromethylated styrene-divinylbenzene copolymer treated with trimethylamine, melamine-guanidine-formaldehyde polymers, urea-formaldehyde-triethanolamine resins, polyalkylene-polyamine-formaldehyde resins, etc.

The metals that may be introduced into the ion exchange resins are preferably those of Groups IB and VIII of the periodic table, and more preferably those of the platinum series, i.e. platinum, palladium, ruthenium, rhodium, osmium and iridium. Metal compounds, preferably those that are soluble in water or other solvent, that may be introduced in the resins are compounds of such metals as iron, cobalt, nickel, ruthenium, rhodium, palladium, osmium, iridium, platinum, copper, silver, gold, manganese, rhenium, chromium, molybdenum, tungsten, vanadium, niobium, tantalum, titanium, zirconium, hafnium, scandium, yttrium, lanthanum, and actinium. Zinc and cadmium are also of use. Preferred compounds are those of metals of Group VIII, comprising the platinum series and the iron group. Another preferred group are the metals of Group VIB; and also Group IVB. Generally, the metal compound may have any suitable inorganic and/or organic ligands.

Owing to the character of the polyfunctional catalysts, i.e. the fact that the functional groups present, which are the sites of chemical reaction, are disposed within molecular dimensions of each other, thus reducing the problem of diffusion, it has been found possible to carry out reactions of the kind described at very mild conditions of temperature and in the liquid phase. Temperature may thus range from room, or lower, up to about 150° to 180°C. Reaction times are conventional, extending from several seconds to several hours. The reaction may be performed as a flow reaction, either in a fixed bed or a stirred tank reactor, or it may be carried out batchwise. Pressures may be atmospheric and may range higher, if desired, in order to maintain the liquid phase or to increase the reaction rate. Reactant concentrations are conventional. It should be observed that the catalysts are solids, and insoluble in conventional liquids, thus permitting liquid reactants and products to be separated therefrom by conventional filtration, decantation, or centrifugation.

Turning now to the reaction products, they may in many cases be unexpected; and where expected, they are obtainable under milder conditions and with less likelihood of undesirable by-products. For example, a ketone may be reacted in the presence of hydrogen and an alcohol over a platinum-containing cation exchange resin having sulfonic acid groups to give an ether, the alcohol being added to the ketone; with a physical mixture of particles of the original cation exchange resin (without platinum) and particles of a conventional platinum-on-alumina catalyst, no ether was obtained, the product being an alcohol corresponding to the reduction product of the ketone. In another case, a cycloalkanone was reacted in the presence of hydrogen with a carboxylic acid over the same polyfunctional catalyst to give a cycloalkyl ester of the acid; with the same physical mixture of resin and platinum-on-alumina particles, the product was a cycloalkanol, comprising the reduction product of the cycloalkanone. For illustrative purposes it may be helpful to set forth by equations the first described of these examples. Thus, with R and R' equal to alkyl, the reaction mechanism may be written as follows:

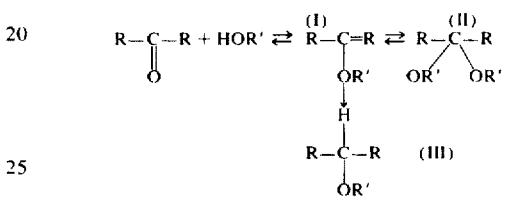

It is considered that the ketone reacts with the alcohol, in the presence of the catalyst to give an intermediate product (I) which reacts to form product (II). In the presence of hydrogen, the intermediate (I) forms the desired product (III) which is an ether. The reaction steps resulting in formation of (I) and (II) are additive reactions, and are catalyzed by acid sites; the step resulting in (III) is a hydrogenation and is catalyzed by metal sites. The reaction, which is also described below in Example 1, proceeds at 50°C. With acetone and methanol as the reactants, the steady state concentration of (I) was less than 0.01 molar. In view of this low concentration of the intermediate, and in further view of the low diffusion rates known to prevail in the liquid phase, the formation of product (III) is regarded as unpredictable and to have been influenced by the fact that the acid and metal sites of the catalyst were in very close proximity, as described. Thus, the intermediate (I) would not have to diffuse far from an acid site to reach a metal site. The reaction mechanism may be termed a reductive alkylation. When tried with a loose physical mixture of cation exchange resin and platinum-on-alumina particles, no ether product was detected. Of interest is the fact, as illustrated in Example 3, that product (III) may be formed by starting with product (II), using the same polyfunctional catalyst.

In the second of the two examples noted, cyclohexanone and acetic acid were reacted together. The intermediate could not be detected, its concentration being less than 0.001 molar. The product identified was an ester, cyclohexyl acetate, whose formation is regarded as unpredictable. With the same physical mixture of catalysts as that noted in the preceding paragraph, no such ester was detected; rather, cyclohexanol, comprising the reduction product of the starting ketone, was found. The reaction mechanism may be termed a reductive acylation; it is described further in Example 6, where the temperature is shown as ranging from 25° to 84° C.

The foregoing description of the equations and reaction mechanism should be understood as being illustrative and not limiting.

It may be apparent that the invention is of particular utility for the conduct of catalytic polystep reactions wherein the first reaction step, or even a subsequent step, is substantially limited in respect of the conversion attainable, i.e., where the step produces an intermediate product in low concentration, say less than 5% or 1% or 0.1%, or even in undetectable concentration. In such a case, the invention makes it possible for this intermediate to enter into a succeeding reaction step by drastically reducing to molecular dimensions the distance over which the intermediate must diffuse to a neighboring reaction site where it may react to form a product at a greater conversion, and where such product may be a desired one or lead to a desired one. The limited reaction step is thus coupled with the succeeding step in that a product of the former is removed for use in the latter; in effect, the rate of the said former or coupled reaction, although low, can be maintained. The realization of a coupled reaction reinforces and enhances the benefit provided by the closely spaced reaction sites, which, as described, are separated only by distances of a molecular order. In the case of some reactions the presence of an intermediate may be unsuspected, but that fact would not prevent the benefits of the invention from being realized. In this connection, it is intended that the term intermediate shall also include a side product.

It should be understood that the invention is not limited to polystep reactions in which an intermediate is present in low concentrations, as it is useful in reactions where the intermediate is produced in substantial amounts. For example, in a reaction involving removal of an alkoxy group and its replacement by hydrogen, the intermediate may be formed in relatively large amounts and may be converted to high yields of a desired product.

A component step of a polystep reaction, or reaction mechanism, may be any one of a number, and may be classified as an elimination, addition, isomerization, or miscellaneous reaction. From the group of elimination reactions, the step may be any one of the following: aromatization; clevage of acetals, acylals, ethers, ketals, etc.; cracking; dealkylation; decarbonylation; decarboxylation; dehalogenation; dehydrohalogenation; dehydrogenation; dehydration; desulfonation; etc. From addition reactions, the step may be one of alkylation; alcohol addition; carbonylation; carboxylic acid addition; condensation; cyclooligomerization; dimerization; esterification; hydroformylation; hydrohalogenation; hydrogenation of carbonyl group-containing compounds; hydrogenation of olefins; hydrogenation of acetylenes; hydrogenation of aromatics; hydrogenation of ester groups; hydrogenation of nitriles; hydrogenation of imines; hydrogenation of nitro groups; hydrogenation of nitroso groups; hydration; polymerization of olefins, diolefins, and acetylenes; thiol addition; hydrocarboxylation; hydroesterification; hydrocyanation of olefins; etc. From the group of isomerization reactions, the step may be enolization; isomerization of paraffins or olefins or aromatics; etc. Or the step may be a miscellaneous reaction such as oxidation; substitution of aromatics and other compounds; vinyl group interchange; transesterification; epoxidation; etc.

In a polystep reaction, two or more of the foregoing enumerated reactions may be involved. Preferred polystep reactions are those catalyzed in one step by acid sites, such as addition of water, alcohols, thiols, and carboxylic acids to olefins, diolefins, or carbonyl compounds; clevage of acetals, acylals, ethers, ketals, etc.; condensation; dehydration; enolization; polymerization; and the like; and in another step by metal sites, such as hydrogenation; dehydrogenation; decarbonylation; oxidation; etc.; or by metal compound sites such as carbonylation; cyclooligomerization; etc. Also preferred are polystep reactions catalyzed in one step by basic sites such as condensation of carbonyl compounds; addition of thiols to olefins; addition to olefins of compounds containing activated methylene groups; etc.; and in another step by metal sites or metal compound sites such as those described.

It will be understood that a variety of polystep reactions are possible, involving not only different reaction steps but also different sequences of steps and different catalytic sites or functions. Several illustrative polystep reactions may be noted, using a simplified form some times described as a reaction scheme, wherein A is a starting reactant; B, C, and D are products which may or may not be desired, including intermediates; P is a desired product; $a$ is an acid site; $b$ is a basic site; $m$ is a metal site; and $mc$ is a metal compound site:

  (1)

  (2)

  (3)

  (4)

  (5)

  (6)

  (7)

Scheme (1) may represent the polystep reaction of Example 6 below, also noted above, where reactant A is cyclohexanone, intermediate B is 1-acetoxycyclohexene, and the desired product P is cyclohexyl acetate.

In scheme (1), if B is an intermediate formed in very low concentration, and if each step were carried out in separate reaction zones, or with a loose physical mixture of catalysts, the formation of product P would be impracticable.

Scheme (7) may represent the polystep reaction of Example 1, also set forth above in equation form, wherein A is acetone, intermediate B is 2-methoxypropene, product C is 2,2-dimethoxypropane, and the desired product P is 2-methoxypropane. Scheme (7) may also represent the reaction of Example 3, wherein C is now the added reactant, 2,2-dimethoxypropane, and B and P are as described.

The particular advantages of the invention are realized in the case of reactions carried out in the liquid phase, i.e., reactions in which, at the temperatures involved, the reactants are in liquid phase by virtue of being either in the liquid state or dissolved in a suitable liquid solvent. This may follow from the fact that liquid phase systems generally exhibit low diffusion coefficients, and this disadvantage is substantially offset by the described catalysts, which provide catalyst sites in such close proximity as to greatly reduce the diffusion path.

The invention may be illustrated by the following examples:

EXAMPLE 1

A dual functional catalyst was prepared by mixing 10 grams (g.) of Amberlyst-15, a cation exchange resin comprising a styrene-divinylbenzene copolymer containing sulfonic acid functional groups, with a solution of 0.5 g. of 1,5-cyclooctadiene-platinum(II) dichloride dissolved in 75 milliliters (ml.) of 2-methoxyethanol over a period of 6 hours at 110° C. The mixture was cooled and filtered, and the solids washed with chloroform and dried in vacuo. Platinum in an amount of 0.68% by weight was found to be distributed as a thin shell on the exterior boundary of the resin particles. This catalyst, in an amount of 1.8 g., was used to catalyze a reaction between methanol and acetone. The reactants were mixed in a mole ratio of 14.6:1 (methanol to acetone) to give a total volume of 40 ml., and this mixture was heated to 50° C. After 40 minutes, hydrogen was introduced and the reaction proceeded for a total of 165 minutes. The following products were identified by vapor phase chromatography (VPC): 2-methoxypropane which was the desired product; 2,2-dimethoxypropane as a side product; and 2-methoxypropene as an intermediate product.

EXAMPLE 2

A single functional catalyst was prepared by suspending 120 ml. of an insoluble intrinsic porous copolymer of styrene-divinylbenzene in a solution composed of 200 ml. of water and 150 ml. of 88% formic acid. To this suspension were added 29 g. of 10% $H_2PtCl_6 \cdot 6H_2O$ solution in water (1.09 g. Pt.). The resultant mixture was stirred and heated to reflux temperature for 1.5 hours. During this time, the platinum was reduced to metal and most of it deposited on the copolymer. The reaction mixture was then cooled and allowed to stand overnight. The copolymer was isolated by filtration and was washed extensively with the following sequence of solvents: water, 1N aqueous sodium hydroxide, water, methanol, and benzene. The resultant catalyst was dried on a rotary evaporator in vacuo and comprised about 1.6% by weight platinum supported on the copolymer of styrene-divinylbenzene.

Methanol and acetone were mixed in a mole ratio of 14.6:1 in an amount to give a total volume of 40 cc. To this solution were added 1.8 g. of the single functional catalyst prepared above. To this solution were also added 1.8 g. of Amberlyst-15, the cation exchange resin comprising a styrene-divinylbenzene copolymer containing sulfonic acid functional groups employed for the preparation of the catalyst in Example 1. Thus, to the solution was added a loose physical mixture of the two catalysts and in this physical mixture the two types of catalytic sites are separated by distances substantially greater than molecular dimensions. The suspension of reactants and catalysts was stirred and heated to 50° C. After 40 minutes, hydrogen was introduced. The reaction was allowed to proceed for 490 minutes at which time a sample was withdrawn and analyzed by VPC. This analysis showed that equilibrium had been established between acetone, methanol, 2,2-dimethoxypropane, and 2-methoxypropene. However, only trace quantities of 2-methoxypropane (the desired product) had been produced. Comparison of these results with those of the dual functional catalyst of Example 1 shows that the dual functional catalyst is far superior to a loose physical mixture of the two catalysts for the reaction described.

EXAMPLE 3

Using the catalyst of Example 1, 64 g. methanol and 10.8 g. 2,2-dimethoxypropane were reacted in the presence of 2-methylbutane as solvent. The mixture was stirred at room temperature (23°C.) and hydrogen was introduced. After 68 minutes the reaction was stopped. VPC analysis showed the presence of 2-methoxypropane.

EXAMPLE 4

A palladium-containing catalyst was prepared by mixing 50 g. of $PdCl_2$, 750 ml. concentrated ammonium hydroxide, and 750 ml. distilled water, heating the mixture to refluxing temperature, then cooling. The mixture was evaporated, the solids washed with absolute alcohol and ether, and filtered. The resulting complex, $Pd(NH_3)_4Cl_2$, in an amount of 5 g., was dissolved in 300 ml. distilled water and then mixed with 140 ml. of wet Amberlyst-15 in the sodium form. The mixture was stirred over a weekend. It was filtered, washed with distilled water, dried, washed with ethanol and ether, and dried at 110°C. for 2 hours. About 10 g. of the product was mixed with 100 ml. of a 22% aqueous solution of hydrazine, and the mixture stirred at 50°C. for 35 minutes, after which it was filtered and washed with water, then with 300 ml. of 6 N HCl solution, then with 1000 ml. of 2 N HCl, then with 2000 ml. water (at which point it was chloride free), then with 500 ml. absolute alcohol and finally with 250 ml. ether. It was dried at 110°C. for 2 hours. The product was the desired catalyst comprising sulfonic acid group-containing resin having zero-valent palladium.

EXAMPLE 5

About 4.88 g. of the palladium-containing Amberlyst-15 catalyst of Example 4 were mixed with 33 ml. methanol and 15 ml. acetone in a 300-ml. Paar vessel and hydrogen introduced. Initially the hydrogen pressure was 50 psi. The reaction continued for 8 hours, with shaking, and then stopped with the hydrogen pressure at 39.5 psi. Initially no heat was applied, the temperature being 25°C.; heat was then applied so that the temperature reached 64°C., and the reaction continued over a period of 8 hours. As determined by VPC, 2-methoxypropane was obtained, the conversion being 40%. It is apparent that the reaction may be run in conventional apparatus at low temperatures and pressures to give a substantial yield of desired product.

EXAMPLE 6

Acetic acid in an amount of 15.1 g. was reacted with 6.1 g. cyclohexanone over the catalyst (0.5 g.) described in Example 1. The reaction started at room temperature (25°C.) in the presence of hydrogen and was stopped after 95 minutes, the temperature reaching a high of 84°C. by application of heat. Cyclohexyl acetate was identified as a reaction product by VPC analysis. This reaction in the presence of Amberlyst-15 resin gives a small amount of 1-acetoxycyclohexene; with conventional platinum-on-alumina catalyst it gives cyclohexanol; and with a loose physical mixture of Amberlyst-15 resin and the conventional platinum-on-alumina, the product is cyclohexanol. By "loose" physical mixture is meant a slurry of the type described in Example 2.

The periodic table classifications as used herein are based on the arrangement distributed by E. H. Sargent & Co., and further identified by the legend "Copyright 1962 Dyna-Slide Co."

By the expression "ion exchange resin" it is intended to include any functional group-containing organic polymer, including the various cation and anion exchange celluloses like carboxymethylated cellulose, oxycellulose, succinic half ester of cellulose, citrate ester of cellulose, sulfoethylated cellulose, phosphorylated cellulose, diethylaminoethyl cellulose, triethylaminoethyl cellulose, and ecteola cellulose comprising material made by reacting epichlorohydrin, triethanolamine, and cellulose in the presence of caustic soda. Also aminoethyl cellulose and N-diethylamino-hydroxypropyl cellulose are included.

It will be understood that the invention is capable of obvious variations without departing from its scope.

In the light of the foregoing description, the following is claimed.

What is claimed is:

1. A method for the production of 2-methoxypropane comprising contacting acetone with methanol in the liquid phase in the presence of hydrogen at a temperature between room temperature and 180°C. and at a pressure sufficient to maintain said acetone and said methanol in the liquid phase, with, as a catalyst, a styrene-divinyl benzene cation exchange resin containing sulfonic acid group acid and a platinum or palladium metal active catalytic cites separated by distances which are of the order of the dimensions of the molecules in the reaction medium, provided however that said acid and metal are in an intraparticle dispersion which cannot be separated from each other by physical means whereby said catalyst was prepared by bringing particles of said resin into contact with a solution containing pi-complex of said metal; decomposing said pi-complex to form elemental metal; and depositing said elemental metal in and on said resin particles to form said intraparticle dispersion.

2. The method of claim 1 wherein said metal is platinum.

3. The method of claim 2 wherein the mole ratio of methanol to acetone is 14.6:1.

4. The method of claim 3 wherein the temperature is 50°C.

5. The method of claim 1 wherein said metal is palladium.

* * * * *